United States Patent
Shibuya et al.

(10) Patent No.: US 9,688,530 B2
(45) Date of Patent: Jun. 27, 2017

(54) INTEGRATED CIRCUIT PACKAGE WITH SENSOR AND METHOD OF MAKING

(71) Applicant: Texas Instruments Incorporated, Dallas, TX (US)

(72) Inventors: Makoto Shibuya, Beppu (JP); Luu Nguyen, San Jose, CA (US); Noboru Nakanishi, Beppu (JP)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 14/723,122

(22) Filed: May 27, 2015

(65) Prior Publication Data
US 2016/0347607 A1    Dec. 1, 2016

(51) Int. Cl.
*B81B 1/00* (2006.01)
*B81B 7/00* (2006.01)
*B81C 1/00* (2006.01)

(52) U.S. Cl.
CPC ........ *B81B 7/0038* (2013.01); *B81C 1/00285* (2013.01); *B81B 2201/0214* (2013.01); *B81B 2203/0338* (2013.01); *B81B 2207/098* (2013.01); *B81C 2203/0154* (2013.01)

(58) Field of Classification Search
CPC .................................................... B81B 7/0061
See application file for complete search history.

(56) References Cited

U.S. PATENT DOCUMENTS

| | | | | |
|---|---|---|---|---|
| 2005/0022594 A1* | 2/2005 | Padmanabhan | ......... | G01F 1/684 73/204.26 |
| 2005/0268712 A1* | 12/2005 | Repko | ................... | G01F 1/6847 73/204.26 |
| 2013/0139584 A1* | 6/2013 | Qasimi | ................. | G01F 1/6842 73/204.21 |

* cited by examiner

*Primary Examiner* — William Harriston
(74) *Attorney, Agent, or Firm* — Rose Alyssa Keagy; Chalrles A. Brill; Frank D. Cimino (57) ABSTRACT

An integrated circuit ("IC") package comprising an IC die having a top surface and a bottom surface, an elongate member having opposite first and second end portions and a mid portion. The mid portion is positioned proximate the top surface of the IC die. The IC package also includes an encapsulant block having a top surface, a bottom surface and opposite first and second lateral side surfaces. The encapsulant block encapsulates the IC die and the elongate member. Either or both of the first and second end portions of the elongate member are exposed.

12 Claims, 10 Drawing Sheets

INTEGRATED CIRCUIT PACKAGE WITH SENSOR AND METHOD OF MAKING

BACKGROUND

Integrated circuit ("IC") packages typically include an integrated circuit die that is mounted on and electrically attached to a leadframe. The electrical connections between the die and leadframe are often made by wire bonding in which a thin conductor wire is bonded at one end to a contact on the die and at the other end to a lead of the leadframe. The leadframe, die and bond wires are usually encapsulated in a protective, nonconductive block of material, such as epoxy. Portions of the leadframe are exposed through the bottom wall and/or sidewalls of the encapsulating block to enable electrical connection of the die to other electronics and/or to facilitate the transfer of heat from the IC die to the surrounding environment.

In an integrated circuit sensor package the die in the package is a sensor die that is adapted to sense a physical parameter of the surroundings of the IC sensor package. For example in a capacitive type humidity sensor a thin polymer film is attached to a surface of an IC die and is connected to electrical circuitry within the die. Changes in humidity affect the amount of moisture absorbed by the polymer film. Moisture absorption causes a change in the capacitance of the film. This change in capacitance is measured by the die circuitry and is representative of the humidity of the air. To make such an IC sensor package, the polymer film attached to the die must be exposed to the surrounding air.

SUMMARY

An integrated circuit ("IC") package including an IC die having a top surface and a bottom surface and an elongate member having opposite first and second end portions and a mid portion. The mid portion of the elongate member is positioned proximate the top surface of the IC die. The IC package includes an encapsulant block having a top surface, a bottom surface and opposite first and second lateral side surfaces. The encapsulant block encapsulates the IC die and the elongate member. At least one of the first and second end portions of the elongate member are exposed.

DETAILED DESCRIPTION

Figure 1:
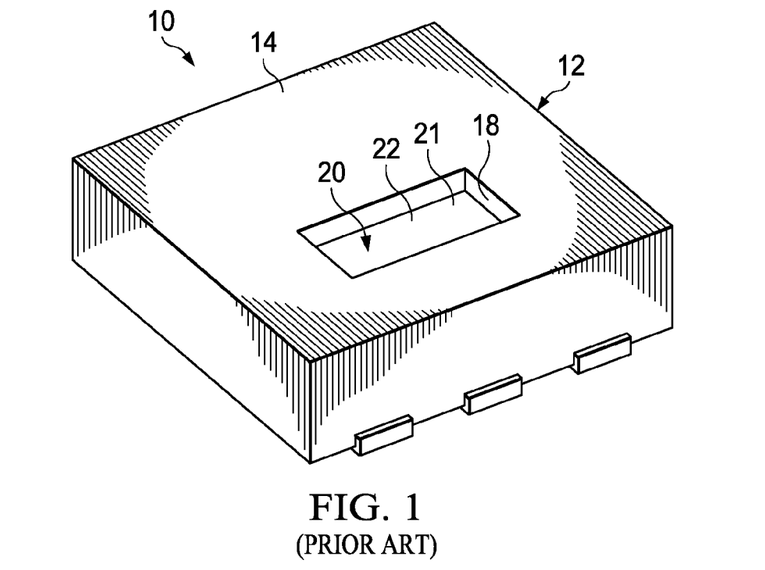
FIG. 1 is an isometric top view of a prior art integrated circuit sensor package.
Figure 2:
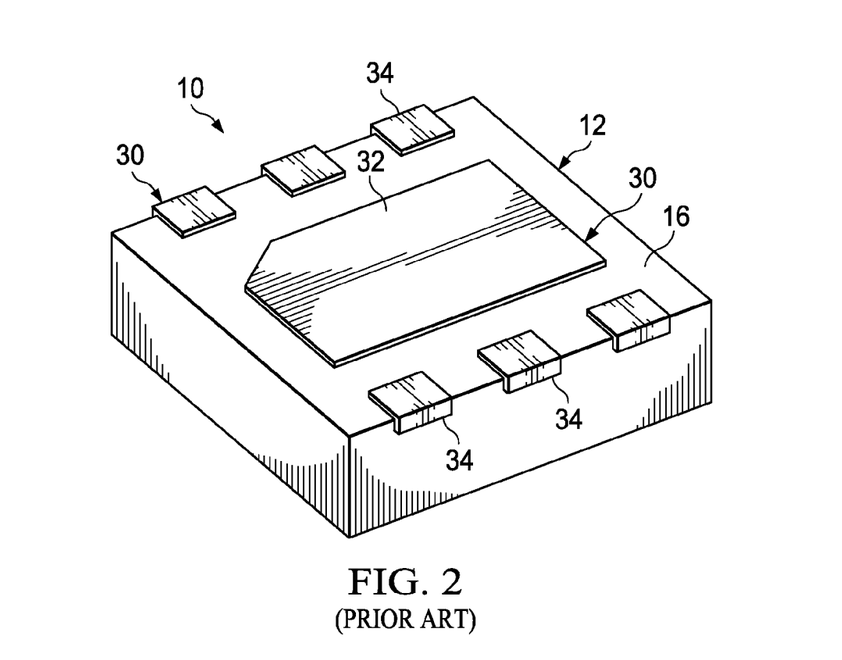
FIG. 2 is an isometric bottom view of the integrated circuit sensor package of FIG. 1.

FIGS. 1 and 2 are top and bottom isometric views of a prior art integrated circuit ("IC") package 10. The IC package 10 includes a generally rectangular box-shaped block 12 of encapsulant, which may be mold compound. The encapsulant block 12 has a top portion 14 and an opposite bottom portion 16. The top portion 14 has a central hole 18 therein, which exposes a top surface portion 22 of an IC die 20. The IC die 20 is mounted on top of a lead frame 30 having a die pad 32 and leads 34. The bottom surfaces of the die pad 32 and leads 34 are exposed at the bottom surface 16 of the encapsulant block 12.

Figure 3:
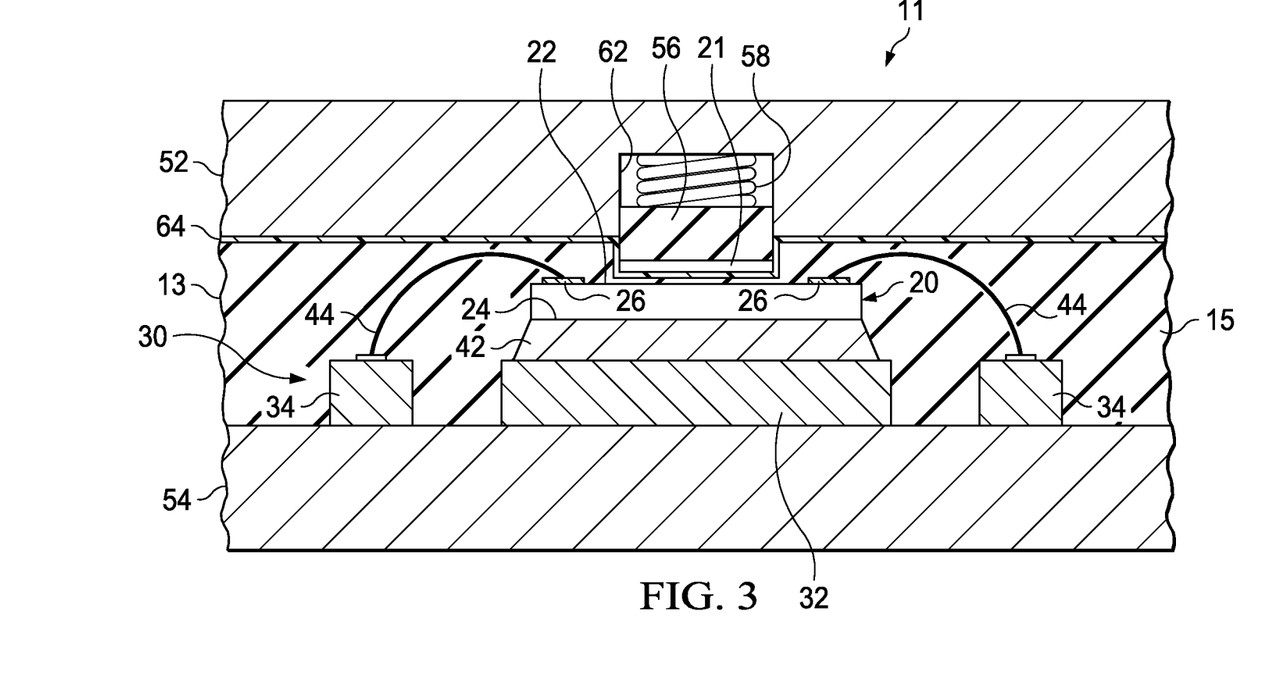
FIG. 3 is a cross-sectional view of a mold assembly in use to produce the integrated circuit sensor package of FIG. 1 and FIG. 2.

FIG. 3 is a cross-sectional elevation view of a mold assembly 11 used to produce the integrated circuit package 10 of FIGS. 1 and 2. FIG. 3 shows what will become the IC package 10, prior to its singulation from adjacent identical IC package units. As shown by FIG. 3, the die pad 32 and leads 34 of the lead frame 30 are supported on a top surface of a bottom mold platen 54 (sometimes referred to in the art as a "mold die"). The IC die 20 is mounted on a top surface of the die pad 32 by attachment medium 42 such as solder or adhesive. Bond wires 44 attached electrical contact pads 26 on a top surface 22 of the IC died 22 to leadframe leads 34.

A top mold platen 52 has a hole 62 extending upwardly from a bottom surface thereof. This hole 62 receives a reciprocal plunger member 56 therein. A spring 58 biases plunger member 56 in a downward direction. When the top mold platen 52 is closed, as illustrated in FIG. 3, the plunger member 56 engages a top surface of the die 20 and remains engaged with it as long as the top platen 52 remains closed.

Prior to closing the top platen member 52, a release film 64 is stretched over the bottom surface thereof. When the mold assembly 11 is in the operating position illustrated in FIG. 3, mold compound 15 is injected into a mold cavity 13 formed between the top and bottom platens 52, 54. The plunger member 56 prevents mold compound 15 from entering the space directly above a central, sensor element portion 21 of the die 20, ultimately forming the hole 18, shown in FIG. 1, above the sensor element 21. The mold compound 15 cools to form the encapsulant block 12. At this point, the top platen 52 is opened and an IC package 10, such as illustrated in FIGS. 1 and 2, is removed. The hole 18 functions to expose the sensing element 21 to air. The hole 18 also enables efficient heat transfer from the sensor die 20 to the surrounding environment.

Such IC sensor packages 10 are relatively expensive to produce. A new mold assembly 11 must be produced for each different IC package design configuration due to the fact that the plunger member 56 must have footprint and location corresponding to that of the sensor element 21. Another sensor die configuration, in which the sensor element is larger and/or at a different location on the top surface of the die, would thus requires a different top platen, Mold assemblies 11 are extremely expensive. Thus a requirement to provide a unique mold assembly 11 for each different die sensor package configuration would considerably increase the overall cost of producing the sensor packages. There is no such requirement for conventional IC packages that do not have sensor dies that must be exposed to the atmosphere. A single mold assembly can be used to produce many different IC package configurations.

Another problem with IC sensor die packages such as IC package 10 is that, because the hole 18 is positioned at the top of the package, it allows dust to collect on the top surface of the sensor element 21 that reduces contact between the sensor element 21 and the atmosphere. The dust can cause inaccuracies in the output of the sensor die 20.

Figure 4:
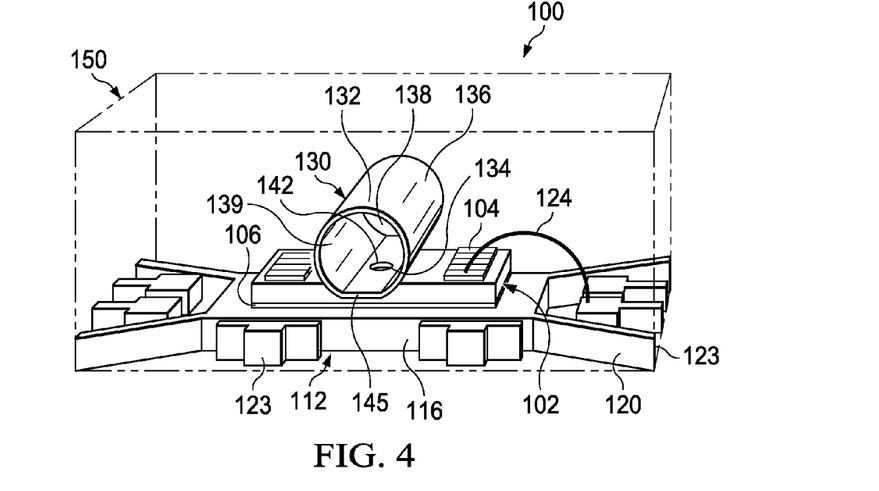
FIG. 4 is an isometric side view of an example embodiment of an integrated circuit sensor package.
Figure 5:
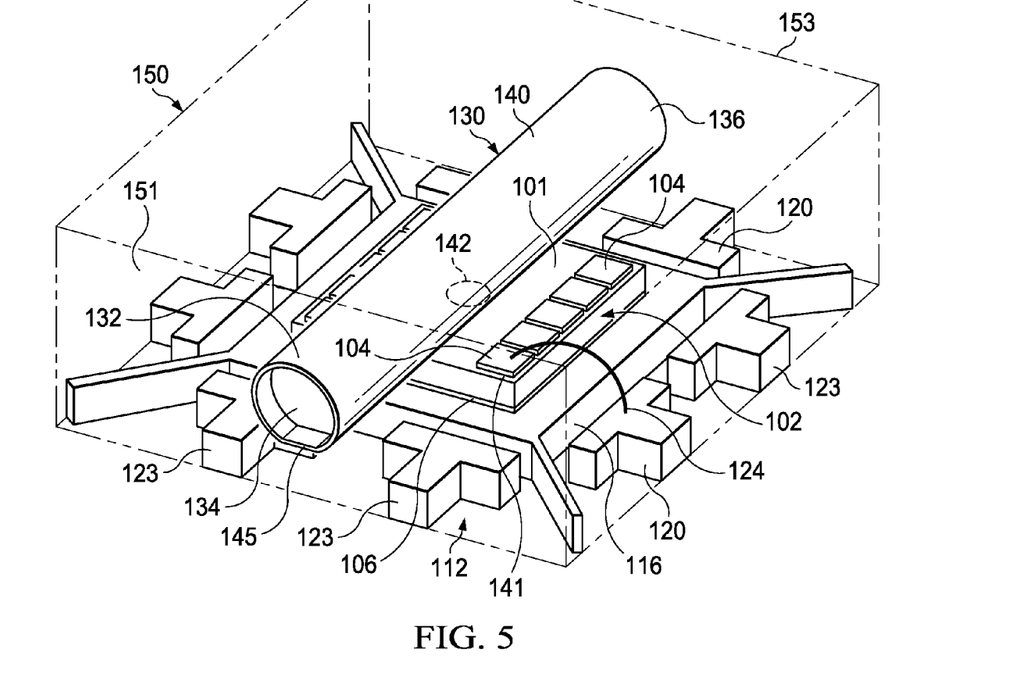
FIG. 5 is an isometric top view of the integrated circuit sensor package of FIG. 4.
Figure 6:
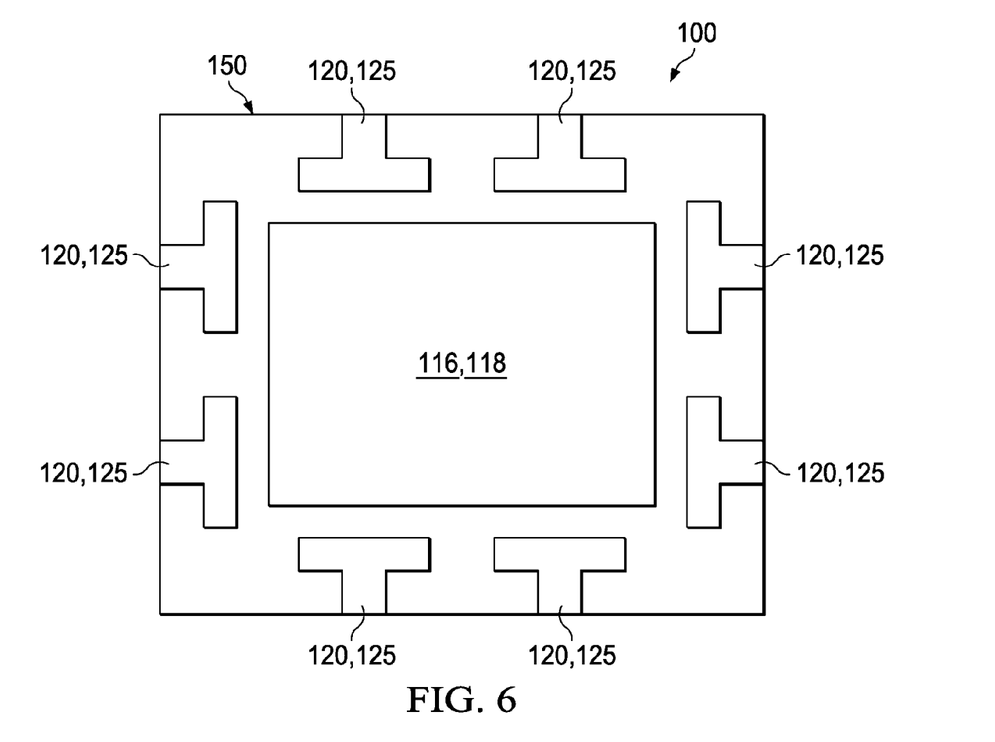
FIG. 6 is a bottom plan view of the integrated circuit sensor package of FIGS. 4 and 5.

FIG. 4 is an isometric side view of an example embodiment of a new integrated circuit package 100. FIG. 5 is a top isometric view and FIG. 6 is a bottom plan view of the integrated circuit package 100. In the illustrated embodiment, the IC package 100 is a quad flat no-leads package ("QFN"). As shown by FIGS. 4 and 5, the IC package 100 includes an IC die 102 having electrical contact pads 104 on a top surface thereof. An attachment medium 106, such as solder or an adhesive material, attaches a bottom surface of the IC die 102 to a leadframe 112.

The leadframe 112 includes a die pad 116 having an exposed bottom surface 118, as shown in FIG. 6. The leadframe 112 also includes a plurality of leads 120. Each lead 120 has a severed side surface 123 and a bottom surface 125 that are exposed through a lateral sidewall and a bottom wall of an encapsulating block of mold compound 150.

Bond wires 124 (only one shown) connect the contact pads 104 on the top surface of the IC die 102 to leads 120, FIGS. 4 and 5.

Figure 10:
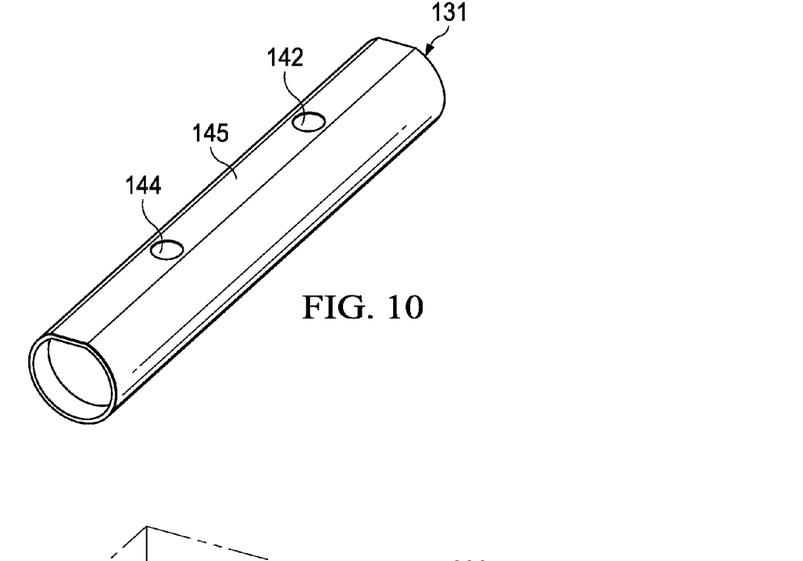
FIG. 10 is an isometric bottom view of one of the tubular members shown in FIG. 9.

As shown in FIGS. 4 and 5, a tubular member 130 has a first end portion 132 with a first end opening 134 and a second end portion 136 with a second end opening 138. A cylindrical passage 139 extends between the two openings 134, 136. The tubular member 130 has a mid portion 140 that has a hole 142 therein. The hole 142 has a central axis extending perpendicular to the central longitudinal axis of the cylindrical passage 139. The tubular member 130 may have a small flat portion 145 on its circumference that engages the top surface of the IC die 102. The hole 142 is formed on this flat portion 145, as best shown in FIG. 4. (This flat surface is also shown in FIG. 10 on a tubular member that has not yet been singulated.) The block 150 of mold compound may be a generally rectangular box-shaped block with flat lateral side surfaces extending between generally flat top and bottom surfaces. The first end 132 of the tubular member 130 terminates flush with one lateral side surface 151 of the mold compound block 150 and the second end 136 terminates flush with the opposite lateral side surface 153 of the encapsulant block. The mid portion 140 of the tubular member rests on a top surface 101 of the IC die 102 above a sensing element 141 on the top surface 101 of the die. The hole 142 is positioned in the flat portion 145 of the tubular member that is above the sensing element 141.

The tubular member 130 and hole 142 therein thus allow the ambient atmosphere, or other gases, to come into contact with the sensor element 141 on the top surface 104 of the IC die 102. Different types of sensor elements 141 are provided for different types of sensors, for example humidity sensors and gas sensors.

Figure 7:
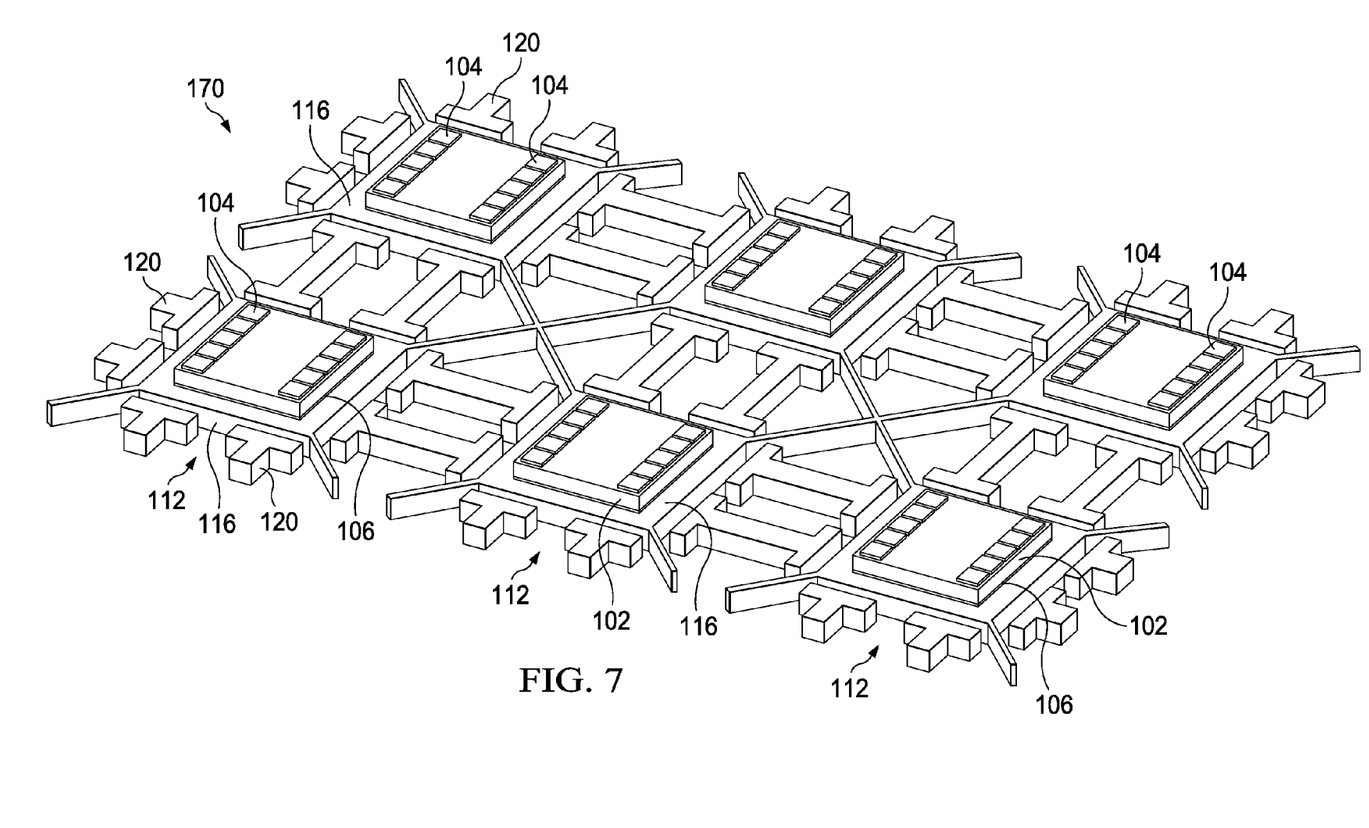
FIG. 7 is an isometric top view of a production assembly including a portion of a lead frame strip with integrated circuit dies mounted on integrally connected lead frame portions of the leadframe strip.
Figure 8:
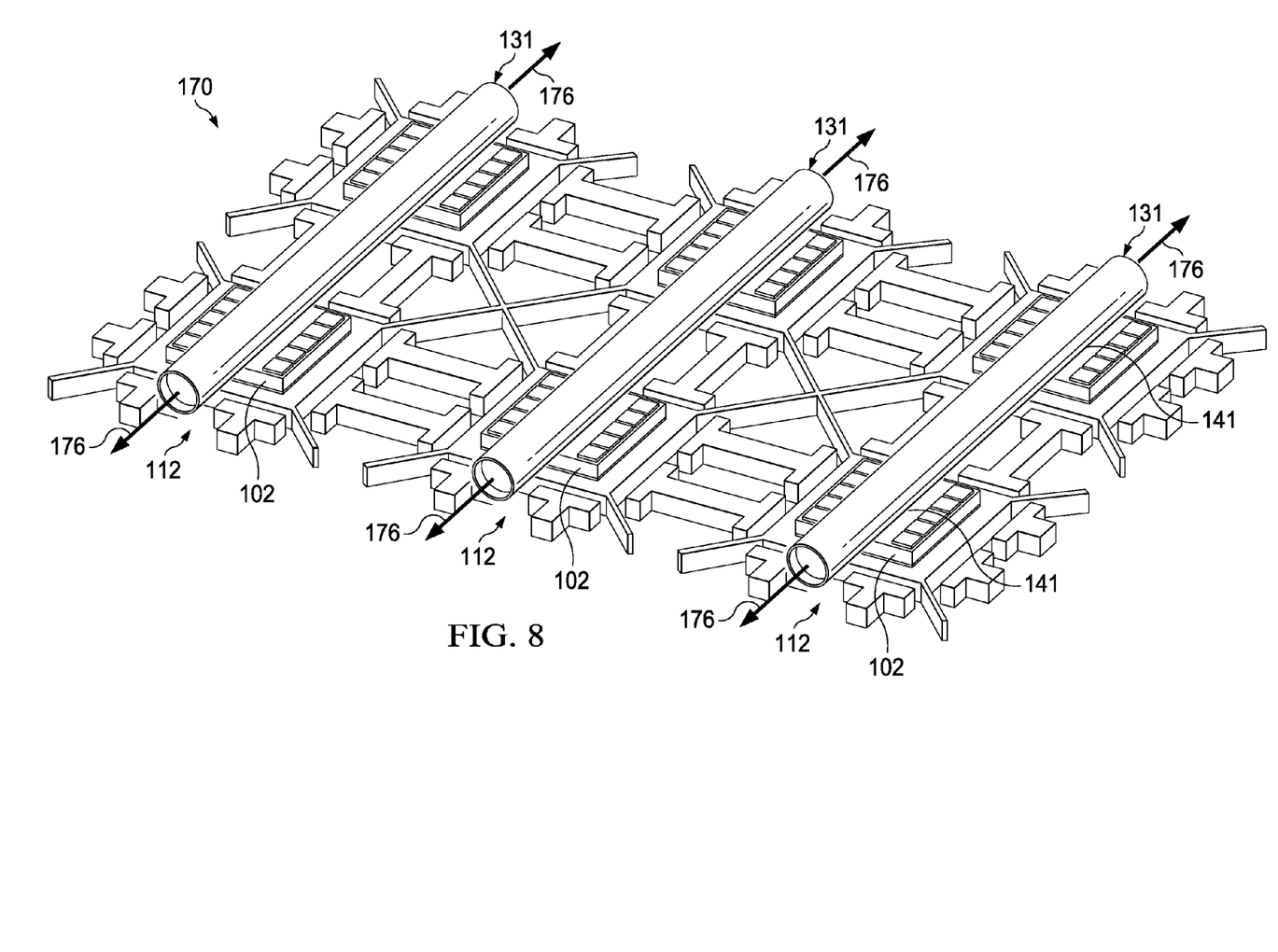
FIG. 8 is an isometric top view of a production assembly like FIG. 7, but further including tubular members engaging the integrated circuit dies.
Figure 9:
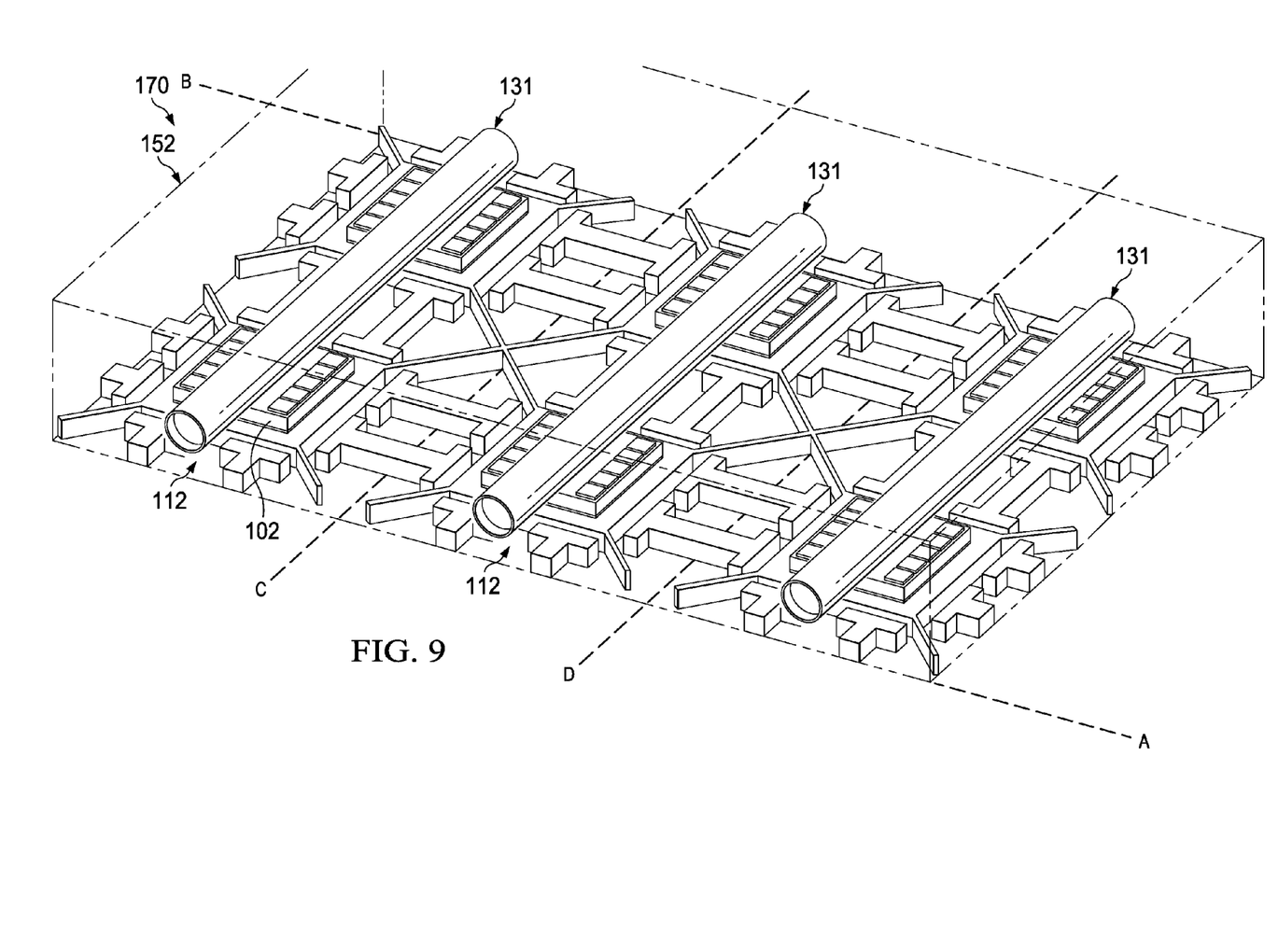
FIG. 9 is a top isometric view of the production assembly of FIG. 8 after molding.

FIGS. 7-9 illustrate various stages in the production of integrated circuit packages 100. FIG. 7 illustrates a lead frame strip 170 that includes a plurality of integrally connected lead frames 112. An IC die 102 is mounted on a die pad 116 of each lead frame 112, by attachment media 106, such as solder or adhesive. A 2×3 leadframe portion of a leadframe strip 170 is illustrated in FIGS. 7-9. It will be understood that the leadframe strip 170 may comprise various leadframe grid configurations. In one embodiment, wire bonding, during which bond wires 124 (FIGS. 4 and 5, not shown in FIGS. 7-9) are connected at opposite ends thereof to IC die contacts 104 and leadframe leads 120, is performed at this stage. Bond wires 124, FIGS. 4 and 5, are not shown in FIGS. 7-9 to avoid clutter.

In FIG. 8, elongate tubular members 131 have open ends and are sufficiently long to extend over all the dies 102 in one row of the lead frame strip 170. The tubular members 131 are held in engagement with each of the dies 102 by an attachment medium such as solder or adhesive. In another embodiment the tubular members 131 are held in the position shown by a vacuum 176 that is applied at the open ends of the tubular members 131. In this embodiment, holes 140, 142, are provided in each tubular member 131 at positions so that the holes 140, 142 will be located over sensing elements 141 in corresponding IC dies 102, as shown in FIG. 8. (This vacuum is held until molding takes place.)

Figures 12, 13:
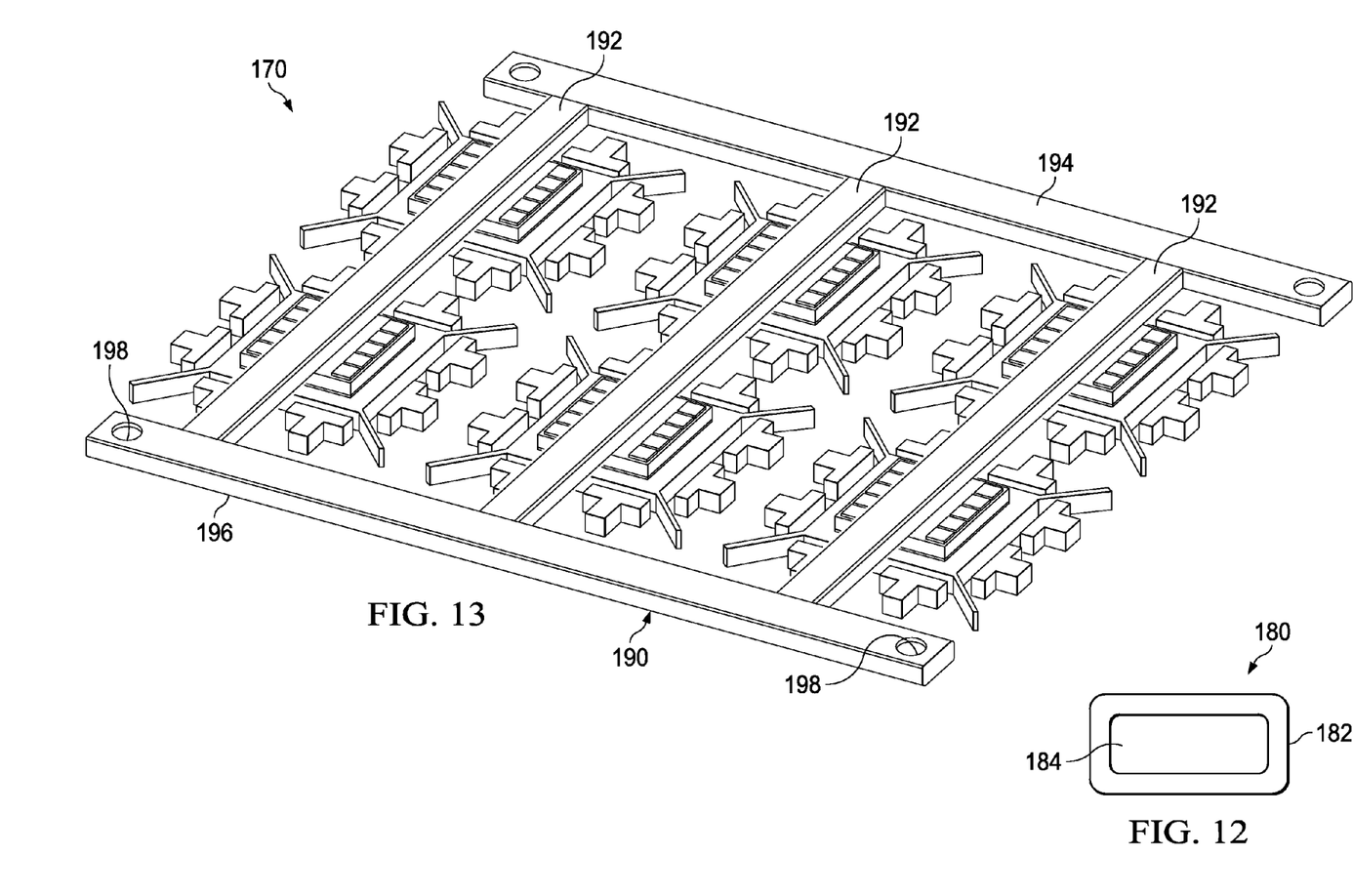
FIG. 12 is an end view of an example embodiment of a tubular member having a rectangular cross section.
FIG. 13 is an isometric view of an integrally connected array of tubular members.

FIG. 12 illustrates an example embodiment of a tubular member 180. In this embodiment the tubular member has a rectangular tubular wall 182 defining a rectangular fluid passage 184 therethrough. The flat bottom surface of the tubular wall may facilitate mounting of the tubular member on respective dies. The tubular member 180 contains a hole positionable over each associated die, like the holes 142, 144 provided in the bottom surface of the tubular member 170, FIG. 10. The rectangular tubular member 180 may be mounted and singulated, etc., like the tubular member 170 as described below.

Next, as illustrated in FIG. 9, the entire lead frame strip 170 and attached components are molded to form an unsingulated mold compound slab 152 around the leadframe strip 170, dies 102 and tubular members 131. This slab 152 is then singulated along saw streets AA, BB, CC and DD, as by conventional singulation means, such as singulation saws or stealth lasers. This singulation separates the assembly shown in FIG. 9 into individual IC packages 100 as illustrated in FIGS. 4-6.

Figure 11:
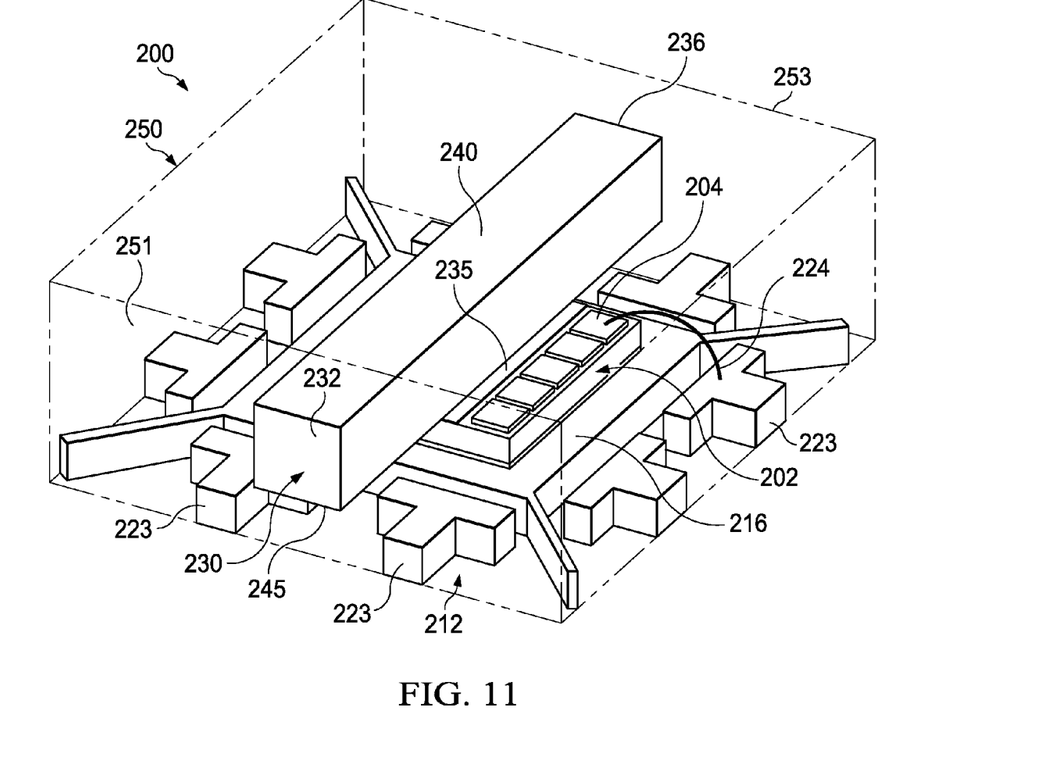
FIG. 11 is an isometric top view of another example embodiment of an integrated circuit sensor package.

FIG. 11 is an isometric top view of another example embodiment of an integrated circuit sensor package 200. In the illustrated embodiment of FIG. 11, the IC sensor package 200 is a quad flat no-leads package ("QFN"). The IC sensor package 200 includes an IC die 202 having electrical contact pads 204 on a top surface thereof. An attachment medium (not shown), such as solder or an adhesive material, attaches a bottom surface of the IC die 202 to a leadframe 212.

The leadframe 212 includes a die pad 216 having an exposed bottom surface, which may be identical to surface 118 of die pad 116, as shown in FIG. 6. The leadframe 212 also includes a plurality of leads 220. Each lead 220 has an exposed severed side surface 223. Each lead 220 also has an exposed bottom surface 225, which may be identical to the bottom surfaces 125 of leads 120 shown in FIG. 6. The severed side surfaces 223 and bottom surfaces 225 of the leads 220 are exposed through an encapsulating block of mold compound 250.

Bond wires 224 (only one shown) connect the contact pads 204 on the top surface of the IC die 202 to leads 220.

As shown in FIG. 11, an elongate porous member 230 has a first end face 232 and a second end face 236. Because the elongate member 230 is porous, air may pass through it from one end face 232 to the other 234. The air passing through the member 230 and also come into contact with a top surface or a sensing element 235, which in this embodiment is a flat sheet, that is mounted on the top surface of the sensor die 202 and below the elongate porous member 230. The elongate porous member 230 has a mid portion 240 that is aligned with the sensor element 235. The elongate porous member 230 may have a rectangular cross section and a flat longitudinally extending bottom face portion 245 (only a terminal edge is shown in FIG. 11) that engages the top surface of the IC die 102. The first end face 232 of the elongate member 230 terminates flush with one lateral side surface 251 of the mold compound block 250 and the second end 136 terminates flush with the opposite lateral side surface 253 of the encapsulant block 250.

The elongate porous member 230 allows the ambient atmosphere, (or other gases in some use environments), to come into contact with the sensor element 235 on the top surface of the IC die 202. Different types of sensor elements 235 are provided for different types of sensors, for example humidity sensors and gas sensors.

In one embodiment the elongate porous member 230 is made from ePTFE, which is a stretched form of polytetrafluoroethylene ("PTFE") that allows gases to pass through it while preventing liquid penetration. In another embodiment the elongate porous member 230 is made from porous ceramic, which also has gas transmitting and liquid blocking properties. The manner of mounting the elongate porous members 230 on respective dies 202 may be the same as described above for the tubular members 130.

Figure 14:
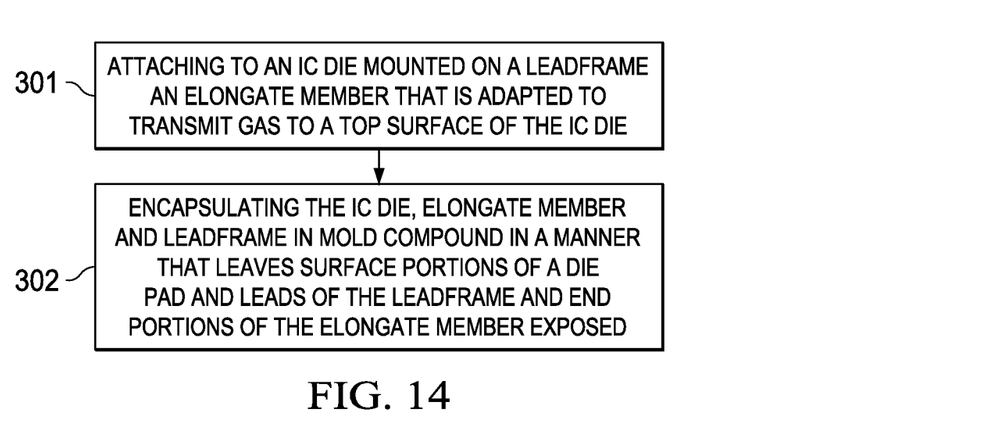
FIG. 14 is a flow diagram of a method of making an integrated circuit sensor package.

An alternative structure for mounting elongate members, e.g., 130, 180, 230, on dies, e.g. 102, 202, is illustrated in FIG. 13. In FIG. 13, tubular members 192 are arranged in a tubular member array 190. In this array the tubular members 192 are connected at opposite ends thereof to a pair of rails 194, 196. The rails may include holes 198 or structure adapted to facilitate handling of the tubular member array 190. Such tubular member arrays may be handled in the same manner as conventional leadframe inserts and enable mounting of multiple tubular members on a leadframe strip at the same time. The rails are trimmed off during singulation of the associated molded slab to form individual IC packages 150, FIGS. 4 and 5. Although an elongate tubular member 170 having a circular cross section is illustrated in FIG. 13, a similar elongate member array could be formed with any of the elongate member geometric cross sectional configurations and material types, e.g. tubular or porous, disclosed herein A flowchart illustrating a method of making an integrated circuit package is shown in FIG. 14. The method includes as shown at block 301, attaching to an 1C die mounted on a leadframe an elongate member that is adapted to transmit gas to a top surface of the 1C die. The method also includes, as shown at block 302, encapsulating the IC die, elongate member and leadframe in mold compound in a manner that leaves surface portions of a die pad and leads of the leadframe and end portions of the elongate member exposed.

Figure 15:
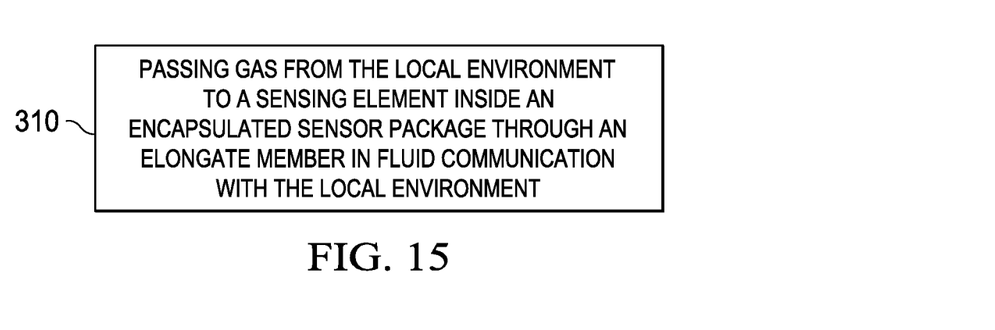
FIG. 15 is a flow diagram of a method of determining the value of a parameter of atmospheric air with an encapsulated integrated circuit sensor assembly.

FIG. 15 is a flow diagram of a method of determining the value of a parameter of gas in a local environment with an encapsulated integrated circuit sensor assembly. The method includes, as shown at block 310, passing gas from the local environment to a sensing element inside the encapsulated sensor assembly through an elongate member in fluid communication with the local environment.

Example embodiments of integrated circuit sensor packages and associated methods of making and using such integrated circuit sensor packages are described in detain herein. Alternative embodiments of such integrated circuit sensor packages and associated methods will occur to those skilled in the art after reading this disclosure. It is intended that the language of the claims be broadly construed to cover such alternative embodiments, except as limited by the prior art.

What is claimed is:

1. An integrated circuit ("IC") package comprising:
an IC die having a top surface and a bottom surface;
an elongate member having opposite first and second end portions and a mid portion, said mid portion positioned proximate said top surface of said IC die; and
an encapsulant block having a top surface, a bottom surface and opposite first and second lateral side faces, said encapsulant block encapsulating said IC die and said elongate member in a sealed block of homogeneous material with at least one of said first and second end portions of said elongate member exposed, the at least one of said first and second end portions of said elongate member terminating flush with one of said opposite first and second lateral side faces.

2. The IC package of claim 1, said IC die comprising a sensor die having a sensing element on said top surface thereof, said elongate member being constructed and arranged to transmit gas therethrough to said sensing element.

3. The IC package of claim 1 wherein both of said first and second end portions of said elongate member are exposed at opposite lateral side surfaces of said encapsulant block.

4. The IC package of claim 1 wherein said elongate member is a tubular member.

5. The IC package of claim 4 wherein said tubular member has at least one hole in said mid portion thereof.

6. The IC package of claim 4 wherein said tubular member is constructed from at least one of: carbon-nylon composite, epoxy resin and fluorine-containing rubber.

7. The IC package of claim 2 wherein said tubular member defines a fluid passage extending between said first and second end portions thereof.

8. The IC package of claim 1 wherein said elongate member is a porous member adapted to transmit gas therethrough.

9. The IC package of claim 8 wherein said porous member is constructed of polytetrafluoroethylene ("PTFE").

10. The IC package of claim 8 wherein said porous member is constructed of porous ceramic.

11. The IC package of claim 1 further comprising a leadframe having a die pad and a plurality of leads, said IC die bottom surface being attached to said die pad, said die pad and said leads being exposed at said bottom surface of said encapsulant block, wherein said IC die comprises a plurality of electrical contact pads on at least one exterior surface thereof that are wire bonded to at least one of said plurality of leadframe leads.

12. The IC package of claim 1 wherein said encapsulant block is composed of mold compound.

* * * * *